(12) United States Patent (10) Patent No.: US 8,795,337 B2
Wilcox et al. (45) Date of Patent: Aug. 5, 2014

(54) APPARATUS FOR IMPLEMENTING A SPINAL FIXATION SYSTEM WITH SUPPLEMENTAL FIXATION

(75) Inventors: Bryan S. Wilcox, Collierville, TN (US); Benjamin D. Cowan, Memphis, TN (US); Rodney R. Ballard, Lakeland, TN (US); Heather Lindenman, Otterbein, IN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 761 days.

(21) Appl. No.: 12/609,611

(22) Filed: Oct. 30, 2009

(65) Prior Publication Data

US 2011/0106164 A1 May 5, 2011

(51) Int. Cl.
*A61B 17/70* (2006.01)

(52) U.S. Cl.
USPC .......................................................... 606/264

(58) Field of Classification Search
USPC ......... 606/246, 250–253, 259, 260, 264–270, 606/272, 278, 301
See application file for complete search history.

(56) References Cited

U.S. PATENT DOCUMENTS

| | | | |
|---|---|---|---|
| 5,209,752 A | 5/1993 | Ashman et al. | |
| 5,352,226 A | 10/1994 | Lin | |
| 5,380,323 A | 1/1995 | Howland | |
| 5,545,167 A | 8/1996 | Lin | |
| 5,562,661 A | 10/1996 | Yoshimi et al. | |
| 5,562,662 A | 10/1996 | Brumfield et al. | |
| 5,575,791 A | 11/1996 | Lin | |
| 5,609,593 A * | 3/1997 | Errico et al. | 606/276 |
| 5,611,800 A | 3/1997 | Davis et al. | |
| 5,733,286 A * | 3/1998 | Errico et al. | 606/266 |
| 5,741,255 A | 4/1998 | Krag et al. | |
| 5,976,135 A | 11/1999 | Sherman | |
| 6,030,388 A | 2/2000 | Yoshimi et al. | |
| 6,231,575 B1 | 5/2001 | Krag et al. | |
| 6,413,257 B1 | 7/2002 | Lin et al. | |
| 6,685,705 B1 | 2/2004 | Taylor | |
| 6,706,045 B2 | 3/2004 | Lin et al. | |
| 6,755,830 B2 * | 6/2004 | Minfelde et al. | 606/278 |
| RE39,035 E | 3/2006 | Finn et al. | |

* cited by examiner

*Primary Examiner* — Pedro Philogene
*Assistant Examiner* — David Comstock

(57) ABSTRACT

An apparatus for implementing a spinal fixation system with supplemental fixation includes a spinal fixation rod assembly and at least one supplemental fixation device. The spinal fixation rod assembly is adapted to provide primary fixation at a plurality of first fixation points by being secured to a plurality of first vertebral components except not into one of the first vertebral components of the plurality that is in a weakened structural condition and located between other of the first vertebral components of the plurality. The supplemental fixation device is adapted to provide supplemental fixation for the assembly at a second fixation point by being secured to a second vertebral component located adjacent to and offset from the one first vertebral component in the weakened structural condition and also to interconnect with the assembly to provide anchorage and thus additional fixation supplemental to the primary fixation.

20 Claims, 6 Drawing Sheets

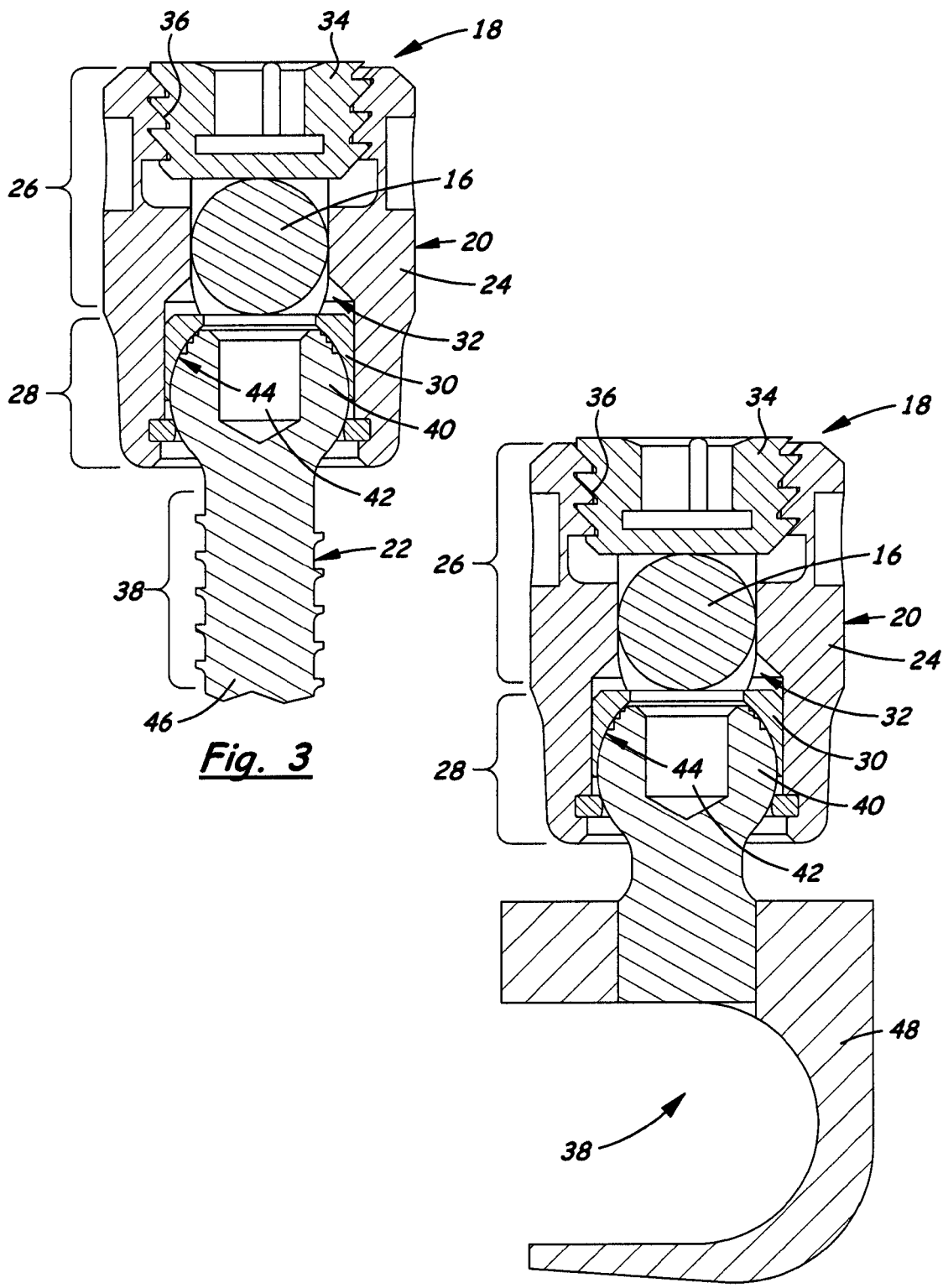

APPARATUS FOR IMPLEMENTING A SPINAL FIXATION SYSTEM WITH SUPPLEMENTAL FIXATION

BACKGROUND

1. Field of the Invention

The present invention relates generally to spinal fixation systems and, more particularly, to an apparatus for implementing a spinal fixation system with supplemental fixation.

2. Description of the Related Art

Spinal fixation systems typically employ a spinal rod for supporting the spine and properly positioning vertebrae of the spine for various treatment purposes. Devices such as bolts, screws, clamps and hooks are typically secured to the vertebrae for connection to the supporting spinal rod. Examples of some known spinal fixation systems are disclosed in U.S. Pat. Nos. 5,209,752 and 5,562,662.

With most spinal conditions to be corrected, surgeons can typically anticipate that the vertebral components where these devices are to be implanted or attached will normally have sufficient strength and integrity to accommodate the devices. However, this is not the typical situation surgeons face in the case of patients with osteoporotic bone conditions. Uncertainty regarding the strength of vertebrae is always present in patients with osteoporotic bone. Oftentimes one vertebral component, such as one pedicle of a plurality thereof where a particular level of fixation is planned, may have a lateral aspect that is not strong enough to hold the intended correction.

Thus, there is a need for an innovation that will compensate for this frequently encountered condition of variable vertebrae strength in order to ensure continued use of spinal fixation systems appropriate in patients with osteoporotic bone conditions.

SUMMARY OF THE INVENTION

The present invention meets this need by providing an innovation that works around the weakened vertebral component, such as a pedicle, and enhances the spinal fixation system by employing supplemental fixation from an adjacent vertebral component, such as a lamina, on the same vertebrae as the pedicle. The innovation relates to a supplemental fixation device employed in the spine fixation system to augment the fixation strength of a spinal fixation rod assembly by providing additional or supplemental fixation at a secondary fixation point located in the adjacent lamina offset from the alignment of the primary fixation points of the spinal fixation rod assembly in the remaining pedicles on either side of the weakened pedicle. This innovation will allow additional construct strength especially for those patients that have osteoporotic bone. Use of the supplemental device further allows the spinal fixation rod to maintain the traditional trajectory of the top-loading, top-tightening spinal fixation system.

Accordingly, in an aspect of the present invention, an apparatus for implementing a spinal fixation system with supplemental fixation employs a plurality of anchor members, a spinal fixation rod, and a supplemental fixation device. Each anchor member includes a coupler having an upper portion adapted to be secured on a spinal fixation rod of the assembly and a lower portion forming a first joint part. Each anchor member also includes an anchor having a lower portion adapted to be anchored to one of a plurality of first vertebral components of a spine and an upper portion forming a second joint part mated with the first joint part so as to form a joint therewith defining a multi-axial pivotal relationship between the anchor and coupler. The supplemental fixation device includes another anchor member and a fixation rod connector. The anchor member of the device includes a coupler having an upper portion and a lower portion forming a first joint part, and an anchor having a lower portion adapted to be anchored to a second vertebral component of the spine and an upper portion forming a second joint part mated with the first joint part so as to form a joint therewith defining a multi-axial pivot relationship between the anchor and coupler. The fixation rod connector, adapted to interconnect the anchor member of the device with a spinal fixation rod of the assembly to provide supplemental fixation, includes an extension coupler adapted to be secured on the spinal fixation rod, and an extension member having a first end portion adapted to be connected to the upper portion of the coupler and extend laterally thereof to a second end portion, the extension coupler being adapted to be connected with the second end portion of the extension member.

BRIEF DESCRIPTION OF THE DRAWINGS

Figure 1:
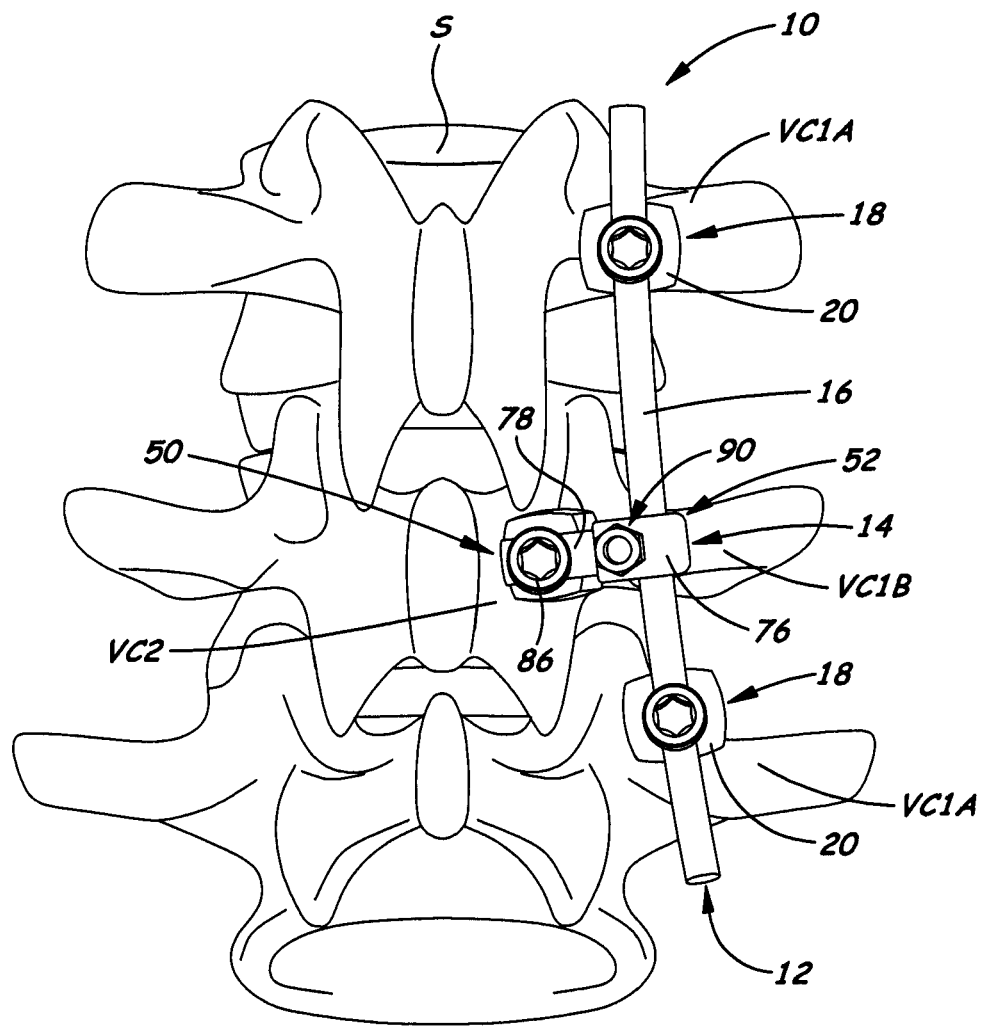

Having thus described the invention in general terms, reference will now be made to the accompanying drawings, which are not necessarily drawn to scale, and wherein:

FIG. 1 is a top view of a spinal fixation system in accordance with the present invention showing an exemplary embodiment of an apparatus for implementing the system with supplemental fixation.

Figure 2:
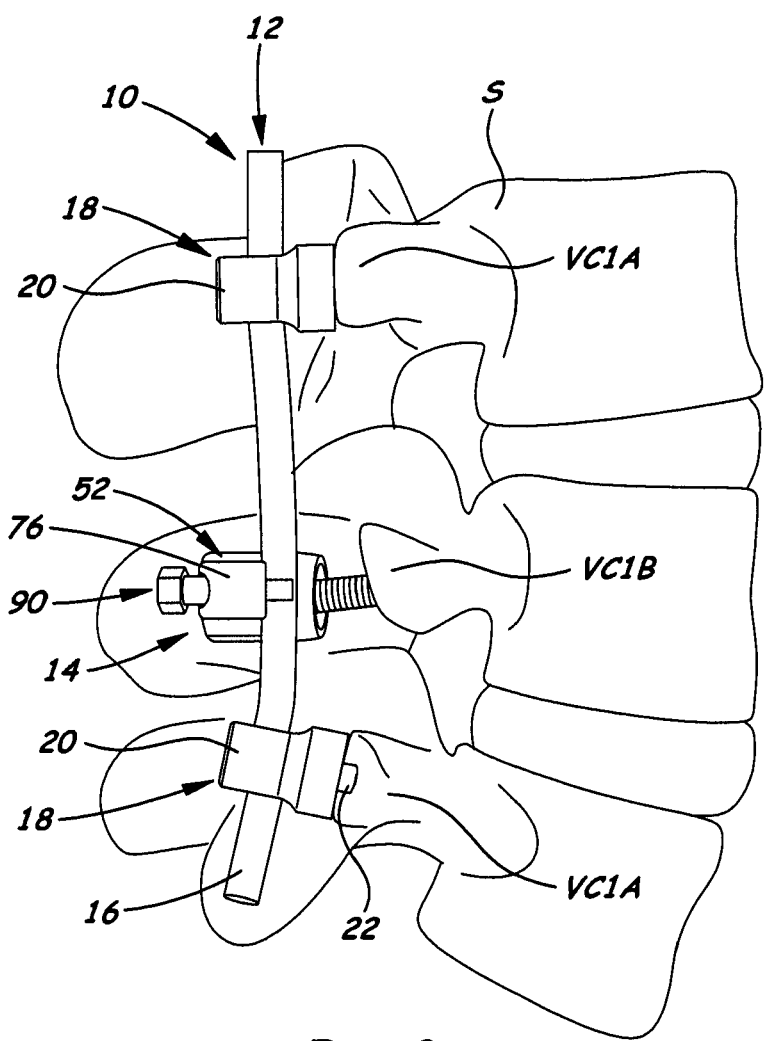

FIG. 2 is a side view of the spinal fixation system of FIG. 1.

FIG. 3 is a partial vertical sectional view of one exemplary embodiment of a first anchor member which may be employed by the apparatus of FIGS. 1 and 2, utilizing an anchor screw.

FIG. 4 is a vertical sectional view of another exemplary embodiment of the first anchor member which may be employed by the apparatus of FIGS. 1 and 2, utilizing an anchor hook.

Figure 5:
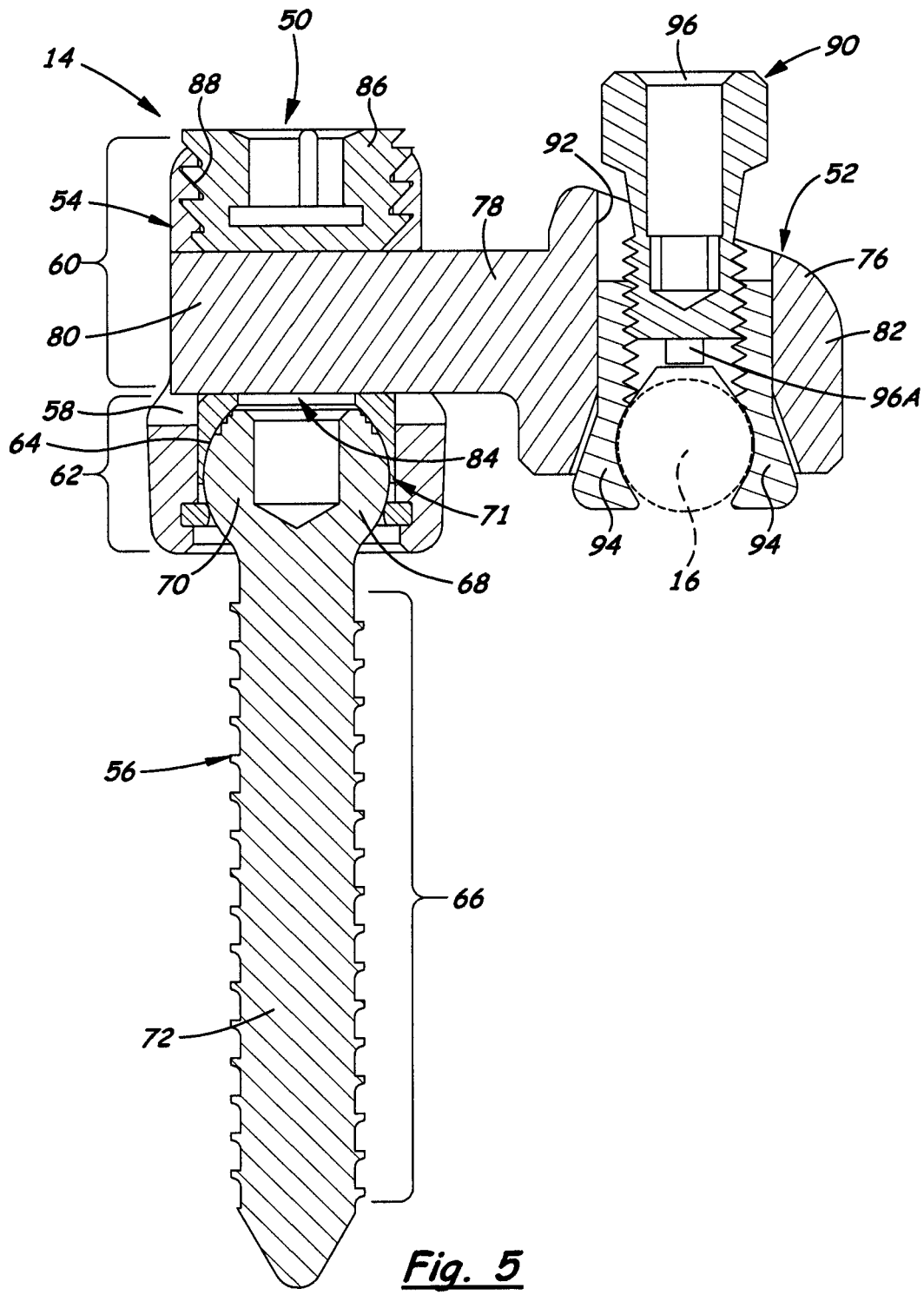

FIG. 5 is a vertical sectional view of one exemplary embodiment of a supplemental fixation device which may be employed by the apparatus of FIGS. 1 and 2, utilizing an anchor screw.

Figure 6:
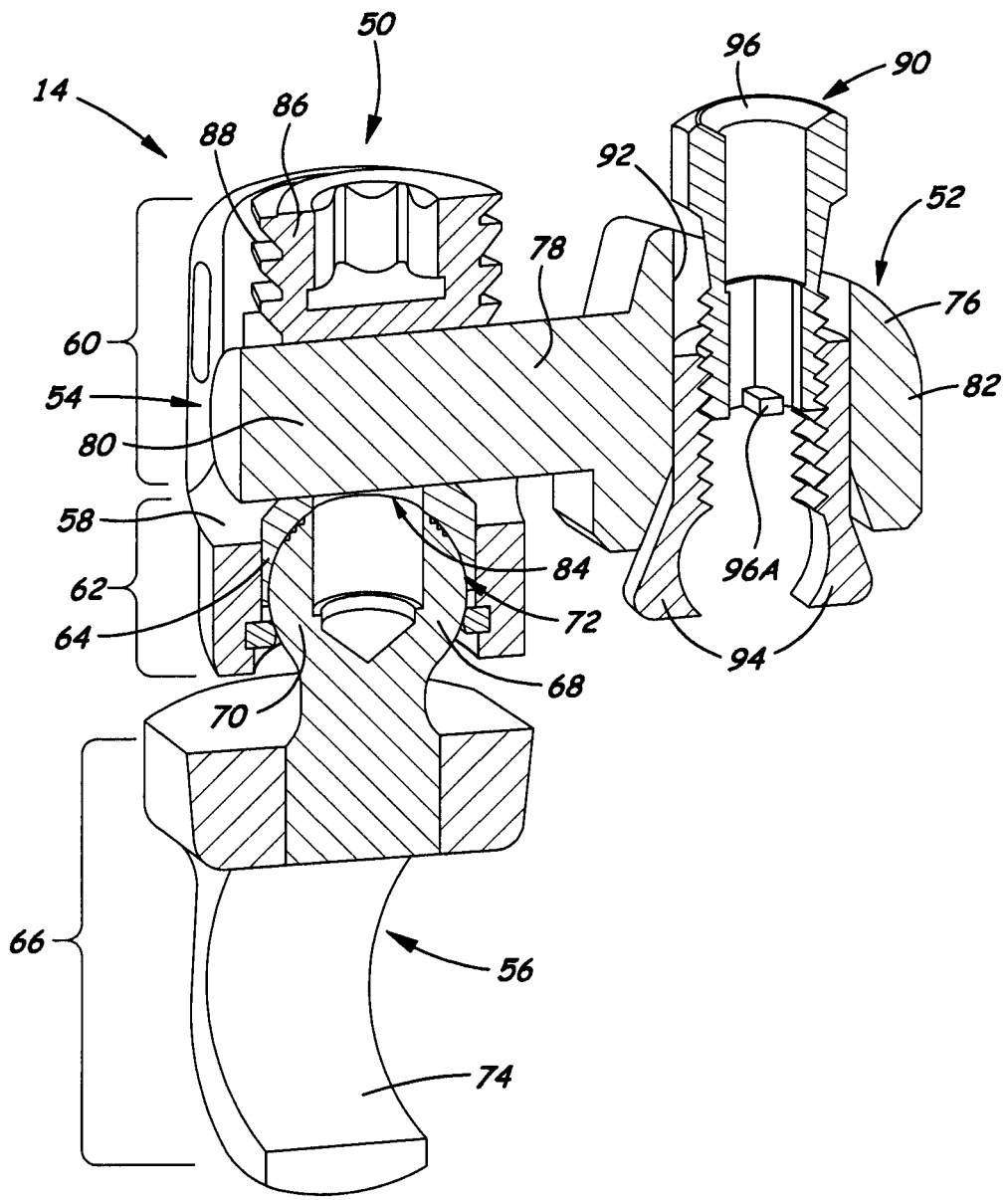

FIG. 6 is a vertical sectional view of another exemplary embodiment of the supplemental fixation device which may be employed by the apparatus of FIGS. 1 and 2, utilizing an anchor hook.

Figure 7:
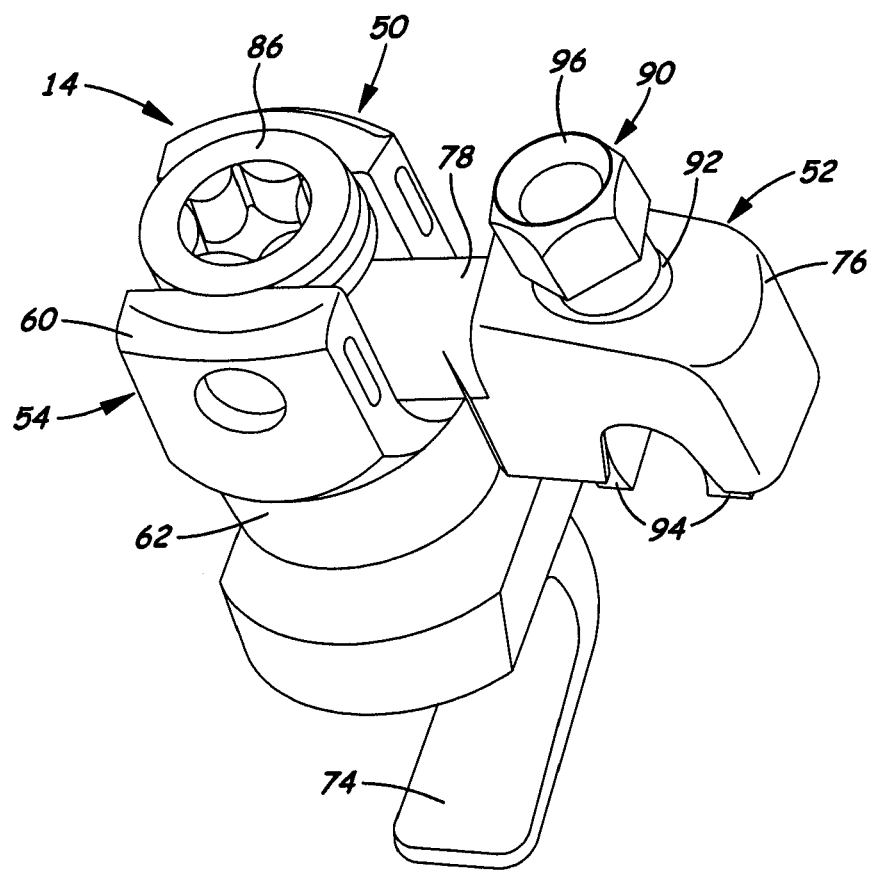

FIG. 7 is a top perspective view of the supplemental fixation device of FIG. 6.

DETAILED DESCRIPTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numerals refer to like elements throughout the views.

Referring now to FIGS. 1 and 2, there is illustrated a spinal fixation system in accordance with the present invention showing an exemplary embodiment of an apparatus, generally designated 10, for implementing the system with supplemental fixation. The implementing apparatus 10 basically includes a spinal fixation rod assembly 12 and at least one supplemental fixation device 14. The spinal fixation rod assembly 12 is adapted to provide primary fixation at a plurality of first fixation loci or points by being anchored to a plurality of first vertebral components VC1A of the spine S except not into one of the first vertebral components VC1B that is in a weakened structural condition and located adjacent to the other of the first vertebral components VC1A. In the exemplary embodiment, the first vertebral components VC1A and VC1B in which the assembly 12 is anchored are vertebral pedicles. The supplemental fixation device 14 is adapted to provide supplemental fixation for the spinal fixation rod assembly 12 at a second fixation locus or point by being anchored to a second vertebral component VC2 of the spine S located adjacent to and offset from the one first vertebral component VC1B in the weakened structural condition. The supplemental fixation device 14 also is adapted to interconnect with the spinal fixation rod assembly 12 to provide anchorage and thus additional fixation supplemental to the primary fixation. In the exemplary embodiment, the second vertebral component VC2 in which the supplemental fixation device 14 is anchored is a vertebral lamina of the same vertebrae that has the weakened vertebral pedicle.

More particularly, referring to FIGS. 1-4, the spinal fixation rod assembly 12 of the implementing apparatus 10 includes a spinal fixation rod 16 and a plurality of first anchor members 18, as best seen in FIGS. 1 and 2. As seen with reference to the one exemplary embodiment in FIG. 3, each of the first anchor members 18 includes a coupler 20 and an anchor 22.

The coupler 20 of each first anchor member 18 has a body 24 with an upper portion 26 adapted to be secured on the spinal fixation rod 16 and a lower portion 28 forming a first joint part 30. More particularly, the body 24 has a transverse bore 32 extending through it and open at its opposite sides (as can be best understood with reference to FIGS. 1 and 2) adapting the body 24 to receive the spinal fixation rod 16 through the body 24. The coupler 20 also has a fastener 34 adapted to thread with a threaded portion 36 of the body 24 and engage the spinal fixation rod 16 so as to secure the spinal fixation rod 16 to the coupler 20 of each first anchor member 18.

The anchor 22 of each first anchor member 18 has a lower portion 38 adapted to be anchored to one of the first vertebral components VC1A of the spine S, such as the vertebral pedicle. The anchor 22 also has an upper portion 40 forming a second joint part 42 mated with the first joint part 30 so as to form a joint 44 therewith defining a multi-axial pivotal relationship between the anchor coupler 20 and the anchor 22. More particularly, the first joint part 30 of the coupler 20 is in the form of a socket and the second joint part 42 of the anchor 22 is in the form of a ball captured in the socket such that the joint is a ball-and-socket joint. Also, as seen in FIG. 3, the lower portion 38 of the anchor 22 of each first anchor member 18 takes the form of a screw-threaded shaft 46 adapted to be implanted into one of the first vertebral components VC1A, such as the vertebral pedicle, at one of the first fixation points. With reference to the other exemplary embodiment of the first anchor member 18, as seen in FIG. 4, all parts are the same as described above with reference to FIG. 3 except that the lower portion 38 of the anchor 22 now takes the form of a hook 48. The hook 48 anchors to, and particularly interfits with, the vertebral pedicle.

Referring now to FIGS. 1, 2 and 5-7, the supplemental fixation device 14 of the implementing apparatus 10 includes a second anchor member 50 and a fixation rod connector 52. As seen with reference to the one exemplary embodiment in FIG. 5, the second anchor member 50 includes a coupler 54 and an anchor 56. The coupler 54 has a body 58 with an upper portion 60 and a lower portion 62, the latter forming a first joint part 64. The anchor 56 has a lower portion 66 adapted to be anchored to the second vertebral component VC2 of the spine S, such as the vertebral lamina. The anchor 56 also has an upper portion 68 forming a second joint part 70 mated with the first joint part 64 so as to form a joint 71 therewith defining a multi-axial pivot relationship between the coupler 54 and anchor 56. More particularly, the first joint part 64 of the coupler 54 is in the form of a socket and the second joint part 70 of the anchor 56 is in the form of a ball captured in the socket such that the joint is a ball-and-socket joint.

Also, as seen in FIG. 5, the lower portion 66 of the anchor 56 of the second anchor member 50 takes the form of a screw-threaded shaft 72 adapted to be implanted into second vertebral components VC2, such as the vertebral lamina, at second fixation point. As seen with reference to the other exemplary embodiment of the second anchor member 50 seen in FIGS. 6 and 7, all parts are the same as described above with reference to FIG. 5, except that the lower portion 66 of the anchor 56 now takes the form of a hook 74. The hook 74 anchors to, and particularly interfits with, the vertebral pedicle.

The fixation rod connector 52 is adapted to interconnect the second anchor member 50 with a spinal fixation rod 16 of the apparatus 10 to provide supplemental fixation. The fixation rod connector 52 includes an extension coupler 76 adapted to be secured on the spinal fixation rod 16. The fixation rod connector 52 also includes an extension member 78 having a first end portion 80 adapted to be connected to the upper portion 60 of the coupler 54 and extend laterally thereof to a second end portion 82. The extension coupler 76 is adapted to be connected with the second end portion 82 of the extension member 78. The body 58 of the coupler 54 of the second anchor member 50 has a transverse bore 84 extending through it and open at its opposite sides (as can be understood with reference to FIGS. 1 and 7). The coupler body 58 is thus adapted to receive the first end portion 80 of the extension member 78 through the bore 84 of the body 58. The coupler 54 also has a fastener 86 adapted to threadably engage a threaded portion 88 of the body 58 and the first end portion 80 of the extension member 78, so as to secure the first end portion 80 of the extension member 78 to the coupler 54 of the second anchor member 50. The fixation rod connector 52 also includes a rod engagement mechanism 90 mounted so as to extend into a bore 92 in the extension coupler 76. The rod engagement mechanism 90 has a pair of jaws 94 which partially encompass the spinal fixation rod 16 and position it for engagement with or disengagement from an inner end 96A of a threaded member 96 when the latter is correspondingly turned in one or the other of opposite directions relative to the jaws 94.

To use the apparatus 10 to implement the spinal fixation system with supplemental fixation, the spinal fixation rod assembly 12 is first fixated to provide primary fixation at the plurality of first fixation loci or points by anchoring the spinal fixation rod assembly 12 to the plurality of first vertebral components VC1A except not to a one first vertebral component VC1B that is in a weakened structural condition. More particularly, anchoring the spinal fixation rod assembly 12 is performed by anchoring the first anchor members 18 on the first vertebral components VC1A, and then installing the spinal fixation rod 16 on the first anchor members 18 so as to extend between and interconnect the first anchor members 18. Also, as mentioned before with reference to FIGS. 1 and 2, the first vertebral components VC1A are vertebral pedicles. At least one supplemental fixation device 14 is fixated next to provide supplemental fixation at a second fixation locus or point by anchoring the supplemental fixation device 14 to the second vertebral component VC2 located adjacent to and offset from the one first vertebral component VC1B in the weakened structural condition. More particularly, anchoring the supplemental fixation device 14 is performed by affixing the anchor 56 to the second vertebral component VC2. Also, as mentioned before with reference to FIGS. 1 and 2, the second vertebral component VC2 is a vertebral lamina of the vertebrae with the weakened vertebral pedicle. The supplemental fixation device 14 is next interconnected with the spinal fixation rod assembly 12 to provide anchorage and thus additional fixation supplemental to the primary fixation.

Use of the above-described supplemental fixation device 14 with its multi-axial joint allows its attachment and adjustment relative to the spinal fixation rod 16 so as to accomplish multiple first and second loci or points of fixation at a single level. The level can still be instrumented even though the lateral aspect of the one pedicle may be blown or the surgeon doesn't feel that the traditional trajectory will be strong enough to hold correction. There can now be provided two types of connections to one spinal fixation rod 16 at the same level thus allowing for enhanced fixation. This ability will allow additional construct strength especially for those patients that have osteoporotic bone. Use of the supplemental fixation device 14 further allows the spinal fixation rod 16 to maintain the traditional trajectory of the top-loading, top-tightening spinal fixation system.

The foregoing description of several embodiments of the invention has been presented for purposes of illustration. It is not intended to be exhaustive or to limit the invention to the precise forms disclosed, and obviously many modifications and variations are possible in light of the above teaching. It is intended that the scope of the invention be defined by the claims appended hereto.

What is claimed is:

1. An apparatus for implementing a spinal fixation system with supplemental fixation, comprising:
    a spinal fixation rod assembly adapted to provide primary fixation at a plurality of first fixation points on a plurality of first vertebral components of a spine, said assembly comprising
        a spinal fixation rod, and
        a plurality of first anchor members connected to said spinal fixation rod and anchored to one of the plurality of first vertebral components; and
    at least one supplemental fixation device adapted to provide supplemental fixation for said spinal fixation rod assembly at a second fixation point on a second vertebral component of the spine, said supplemental fixation device comprising
        a second anchor member anchored to the second vertebral component of the spine located adjacent to and offset from a first vertebral component, said second anchor member including
            a coupler extending along an axis between an upper portion and a lower portion, said lower portion forming a first joint part, said coupler including a transverse bore extending transverse to the axis through the upper portion, and
            an anchor having a lower portion adapted to be anchored to the second vertebral component and an upper portion forming a second joint part mated with said first joint part so as to form a joint therewith defining a multi-axial pivot relationship between said anchor and said coupler of said second anchor member, and
        a fixation rod connector interconnecting said second anchor member with said spinal fixation rod of said spinal fixation rod assembly, said fixation rod connector including
            an extension coupler secured on said spinal fixation rod, a distal end of said extension coupler including jaws which partially encompass the spinal fixation rod, and
            an extension member having a first end portion disposed in said bore of said upper portion of said coupler of said second anchor device such that the extension member is perpendicular to the axis, said extension member extending laterally to a second end portion disposed adjacent to said spinal fixation rod, said extension coupler connected with said second end portion of said extension member.

2. The apparatus of claim 1 wherein each of said first anchor members includes:
    a coupler adapted to be secured on said spinal fixation rod adjacent one of the first fixation points and having a lower portion forming a first joint part; and
    an anchor having a lower portion adapted to be anchored to one of the first vertebral components at one of the first fixation points and an upper portion forming a second joint part mated with said first joint part so as to form a joint therewith defining a multi-axial pivotal relationship between said anchor and said coupler of said each of said first anchor members.

3. The apparatus of claim 2 wherein:
    said first joint part of said coupler is a socket; and
    said second joint part of said anchor is a ball captured in said socket such that said joint is a ball-and-socket joint.

4. The apparatus of claim 2 wherein said anchor of said each of said first anchor members is a screw-threaded shaft adapted to be implanted into one of the first vertebral components at one of the first fixation points.

5. The apparatus of claim 2 wherein said anchor of said each of said first anchor members is a hook adapted to be interfitted to one of the first vertebral components at one of the first fixation points.

6. The apparatus of claim 2 wherein said coupler of said each of said first anchor members includes:
    a fastener adapted to thread with a threaded portion of said body and engage said spinal fixation rod so as to secure said spinal fixation rod to said coupler of said each of said first anchor members.

7. The apparatus of claim 1 wherein said lower portion of said anchor of said second anchor member of said supplemental fixation device is a screw-threaded shaft adapted to be implanted into the second vertebral component at the second fixation point.

8. The apparatus of claim 1 wherein said lower portion of said anchor of said second anchor member of said supplemental fixation device is a hook adapted to be interfitted to the second vertebral component at the second fixation point.

9. The apparatus of claim 1 wherein:
    said first joint part of said coupler of said second anchor member of said supplemental fixation device is a socket; and
    said second joint part of said anchor of said second anchor member is a ball captured in said socket such that said joint is a ball-and-socket joint.

10. The apparatus of claim 1 wherein said coupler of second anchor members includes:
    a body having a transverse bore extending therethrough and adapted to receive said first end portion of said extension member therethrough, and a fastener adapted to thread with a threaded portion of said body and engage said first end portion of said extension member so as to connect said first end portion of said extension member to said coupler of said second anchor member.

11. The apparatus of claim 1 wherein said jaws each include a flange portion at a distal end of each jaw that prevents said spinal fixation rod from moving distally relative to said fixation rod member.

12. The apparatus of claim 1 wherein said jaws define an opening for disposal of said spinal fixation rod, said opening having a maximum diameter that is approximately the same as a diameter of said spinal fixation rod and a minimum diameter that is less than the diameter of said spinal fixation rod to prevent said spinal fixation rod from moving distally relative to said fixation rod member.

13. The apparatus of claim 1 wherein said lower portion of said coupler includes an inner surface defining a circumferential groove extending transverse to the axis, and said coupler includes a retaining member positioned about said upper portion of said anchor and disposed in said groove to prevent said anchor from moving distally relative to said coupler.

14. The apparatus of claim 1 wherein said lower portion of said coupler includes an inner surface defining a channel extending parallel to the axis, said upper portion of said anchor being configured to be inserted into a distal end of said channel.

15. The apparatus of claim 1 wherein at least a portion of said spinal fixation rod is positioned distal to said extension member.

16. A supplemental fixation device for use with a spinal fixation rod assembly, comprising:
an anchor member including
a coupler extending along an axis between an upper portion and a lower portion, said coupler including a transverse bore extending transverse to the axis through the upper portion, the lower portion forming a first joint part, and
an anchor having a lower portion adapted to be anchored to a vertebral component of a spine, and
an upper portion forming a second joint part mated with said first joint part of said coupler so as to form a joint therewith defining a multi-axial pivot relationship between said anchor and said coupler; and
a fixation rod connector interconnecting said anchor member with a spinal fixation rod of the assembly to provide supplemental fixation, said fixation rod connector including
an extension coupler secured on the spinal fixation rod, a distal end of said extension coupler including jaws which partially encompass the spinal fixation rod, and
an extension member having a first end portion disposed in said bore of said upper portion of said coupler such that the extension member is perpendicular to the axis, said extension member extending laterally to a second end portion, said extension coupler connected with said second end portion of said extension member.

17. The device of claim 16 wherein said lower portion of said anchor is a screw-threaded shaft adapted to be implanted into the vertebral component.

18. The device of claim 16 wherein said lower portion of said anchor is a hook adapted to be interfitted to the vertebral component.

19. The device of claim 16 wherein:
said first joint part of said coupler is a socket; and said second joint part of said anchor is a ball captured in said socket such that said joint is a ball-and-socket joint.

20. The device of claim 16 wherein said coupler includes:
a fastener adapted to thread with a threaded portion of said body and engage said first end portion of said extension member so as to connect said first end portion of said extension member to said body.

* * * * *